(12) United States Patent
Hely et al.

(10) Patent No.: US 6,960,176 B1
(45) Date of Patent: Nov. 1, 2005

(54) REINFORCED WRIST BRACE WITH GANG CONNECTED MULTIPLE STRAPS

(75) Inventors: John P. Hely, Oxnard, CA (US); Martha M. Ortega, Oxnard, CA (US)

(73) Assignee: Weber Orthopedic Inc., Santa Paula, CA (US)

(*) Notice: Subject to any disclaimer, the term of this patent is extended or adjusted under 35 U.S.C. 154(b) by 0 days.

(21) Appl. No.: 10/783,008

(22) Filed: Feb. 23, 2004

(51) Int. Cl.$^7$ .............................................. A61F 13/00
(52) U.S. Cl. .............................. 602/21; 602/20; 602/64
(58) Field of Search ............................... 602/5, 20, 21, 602/22, 61, 64; D24/190; 2/162, 170, 16; 128/869, 877, 878, 879

(56) References Cited

U.S. PATENT DOCUMENTS

| | | | |
|---|---|---|---|
| 2,206,404 A | 7/1940 | Jones | |
| 4,854,309 A | 8/1989 | Elsey | |
| 5,307,521 A * | 5/1994 | Davis | ............................. 2/22 |
| 5,415,624 A * | 5/1995 | Williams | ..................... 602/21 |
| 5,769,804 A | 6/1998 | Harris et al. | |
| 5,982,285 A | 11/1999 | Bueche et al. | |
| 6,024,715 A * | 2/2000 | Maxwell | ..................... 602/64 |
| 6,398,748 B1 | 6/2002 | Wilson | |

* cited by examiner

Primary Examiner—Kim M. Lewis
(74) Attorney, Agent, or Firm—William W. Haefliger

(57) ABSTRACT

A wrist brace comprising in combination, a flexible holder to receive the user's wrist and having two flaps adapted to be closed toward one another or toward the wrist to secure the holder about the wrist of the user, a carrier flap on the holder, tightening straps associated with the carrier flap, at the straps having end portions anchored by the carrier, loops on a flap to pass the straps, the straps and carrier having connective material thereon, whereby the straps can be pulled and tightened after passing through said loops, to adjustably press-together on the connective material on the carrier.

20 Claims, 6 Drawing Sheets

Figure 2:
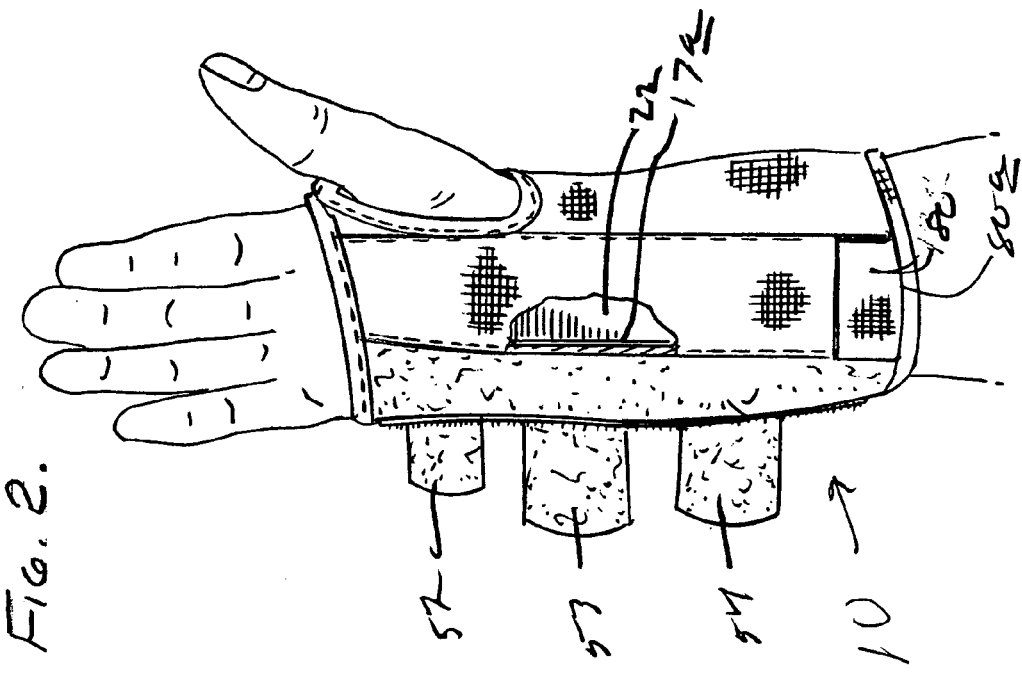

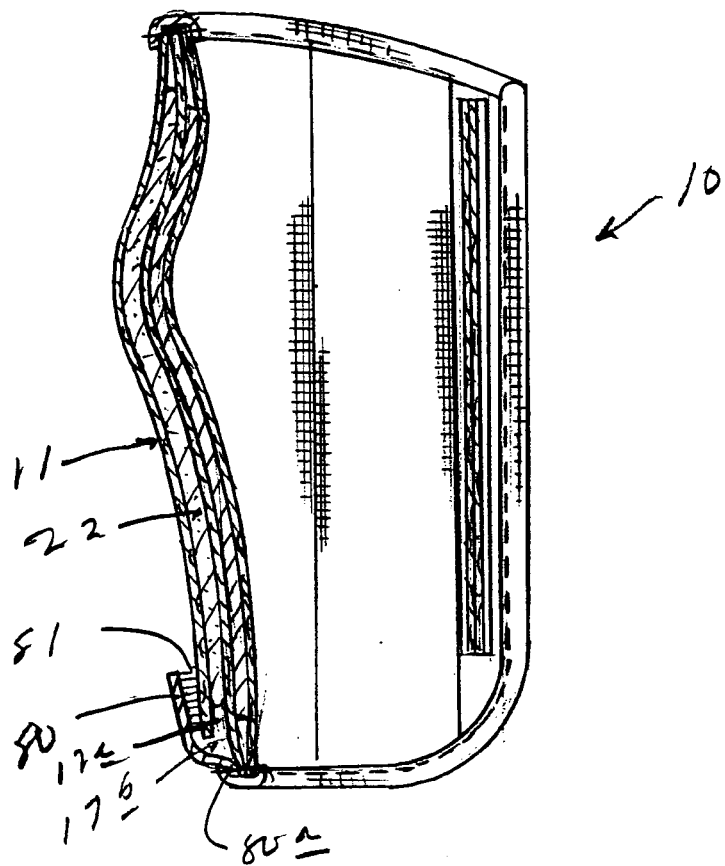
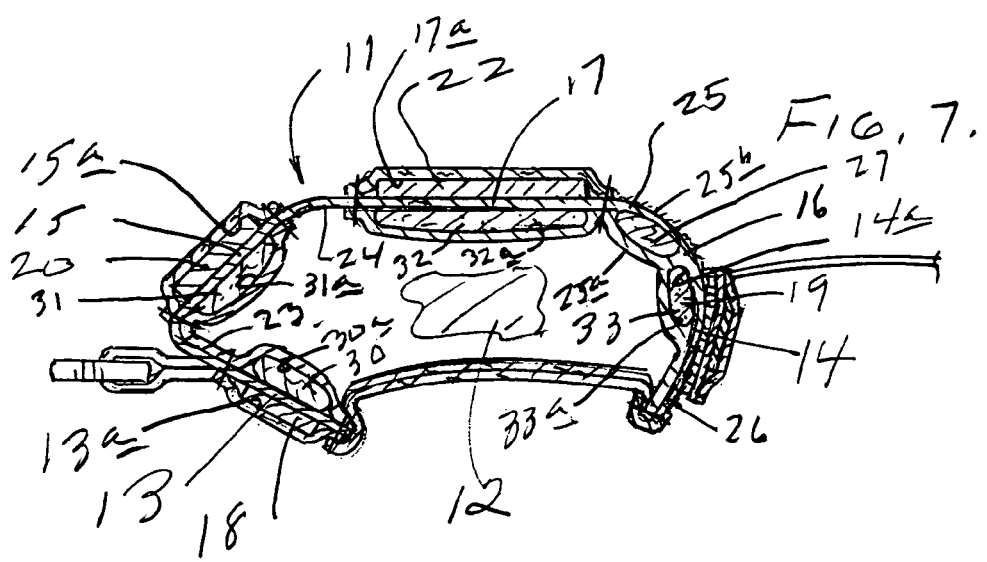

US 6,960,176 B1

REINFORCED WRIST BRACE WITH GANG CONNECTED MULTIPLE STRAPS

BACKGROUND OF THE INVENTION

This invention relates generally to wrist braces, and more particularly to improvements in strap type wrist braces.

There is need for such improvements, enabling ease of attachment to and detachment from the wrist; ease of strap wrapping and tightening with respect to the wrist holder on the brace, for flexibility of that holder, but with local stiffening to be adjustably positioned for wrist bracing in response to wrapping of multiple straps about the holder and over elongated stiffeners; and for maximum comfort to the wrist and thumb of the wearer. There is also need for an improved stiffened brace well adapted to wrists of different sizes and shapes.

SUMMARY OF THE INVENTION

It is a major object of the invention to provide an improved wrist brace meeting the above needs. Basically, the brace comprises:
a) a flexible holder to receive the user's wrist and having two flaps adapted to be closed toward one another or toward the wrist to secure the holder about the wrist of the user,
b) a carrier associated with one flap,
c) tightening straps associated with said carrier, said straps having ends anchored by said carrier,
d) loops on the other flap to pass said straps,
e) the straps and carrier having connective material thereon whereby the straps can be pulled and tightened after passing through said loops, to adjustably press-together on the connective material on the carrier.

As will be seen, preferably three straps are provided at spaced locations along the holder, and may have ends anchored to the carrier which is associated with one of the flaps.

It is another object of the invention to provide a brace wherein the anchored ends of the straps are attached to said carrier at locations spaced along the length of said carrier.

As will be seen, the loops may be aligned lengthwise of the carrier, which itself may comprise an additional flap.

It is a further object to provide at least one stiffener carried by a flap and extending lengthwise to extend beneath all three straps.

At least two such stiffeners are preferably provided to be carried by the holder, the stiffeners spaced apart about a wrist reception zone defined proximate to or by the flaps, whereby flexible holder zones are defined between the stiffeners. At least three such spaced apart stiffeners are preferably provided, along with cushioning material carried by the holder to underlie the stiffeners. Provision is made for selective removal of the stiffeners to obtain desired close fit of the brace to a wrist, or greater brace flexibility.

Yet another object is to provide a flexible auxiliary strap connected to the holder to be adjustably folded over a zone between the user's thumb and forefinger, for adjustable connection to the holder, for firmly attaching the holder in lengthwise position on the wrist.

That auxiliary strap may carry connective material which press attaches to said connective material on the holder.

These and other objects and advantages of the invention, as well as the details of an illustrative preferred embodiment, will be more fully understood from the following specification and drawings, in which:

DRAWING DESCRIPTION

Figure 1:
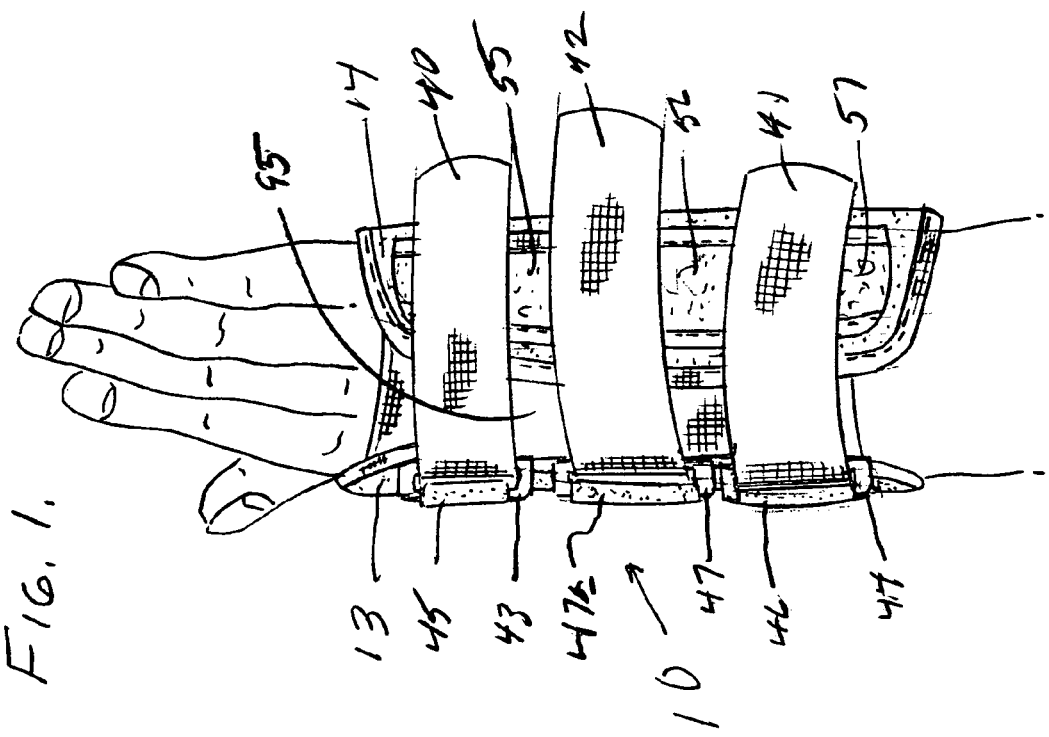
Figure 3:
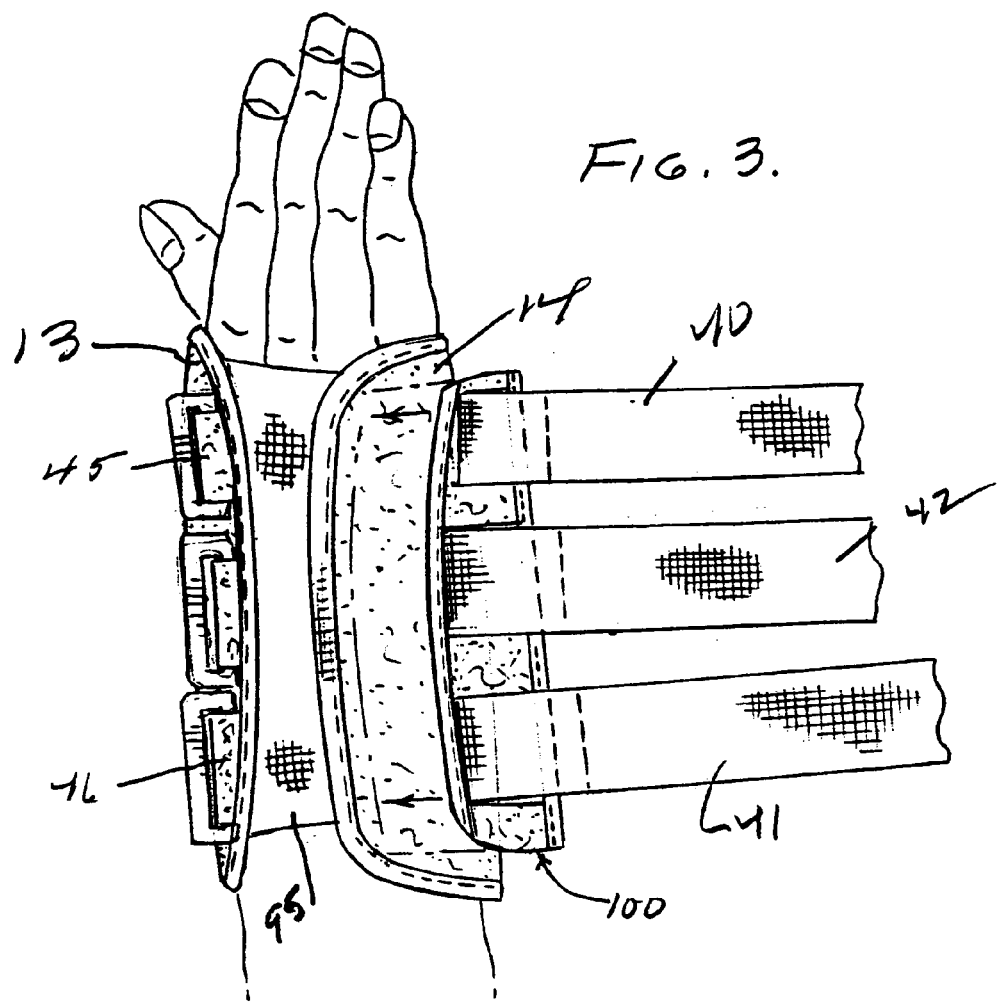
Figure 4:
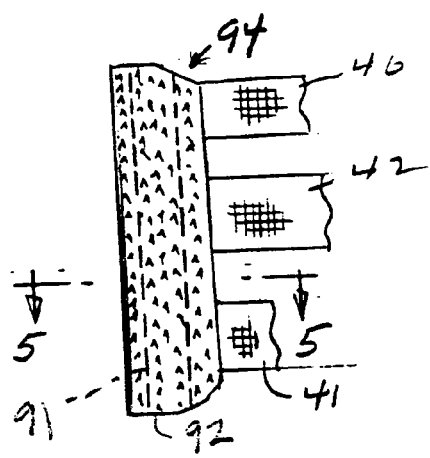
Figure 5:
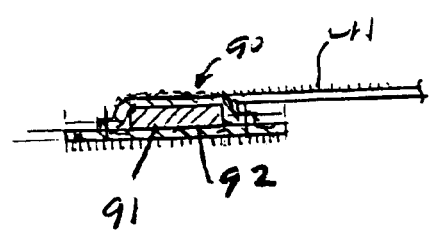
Figure 6:
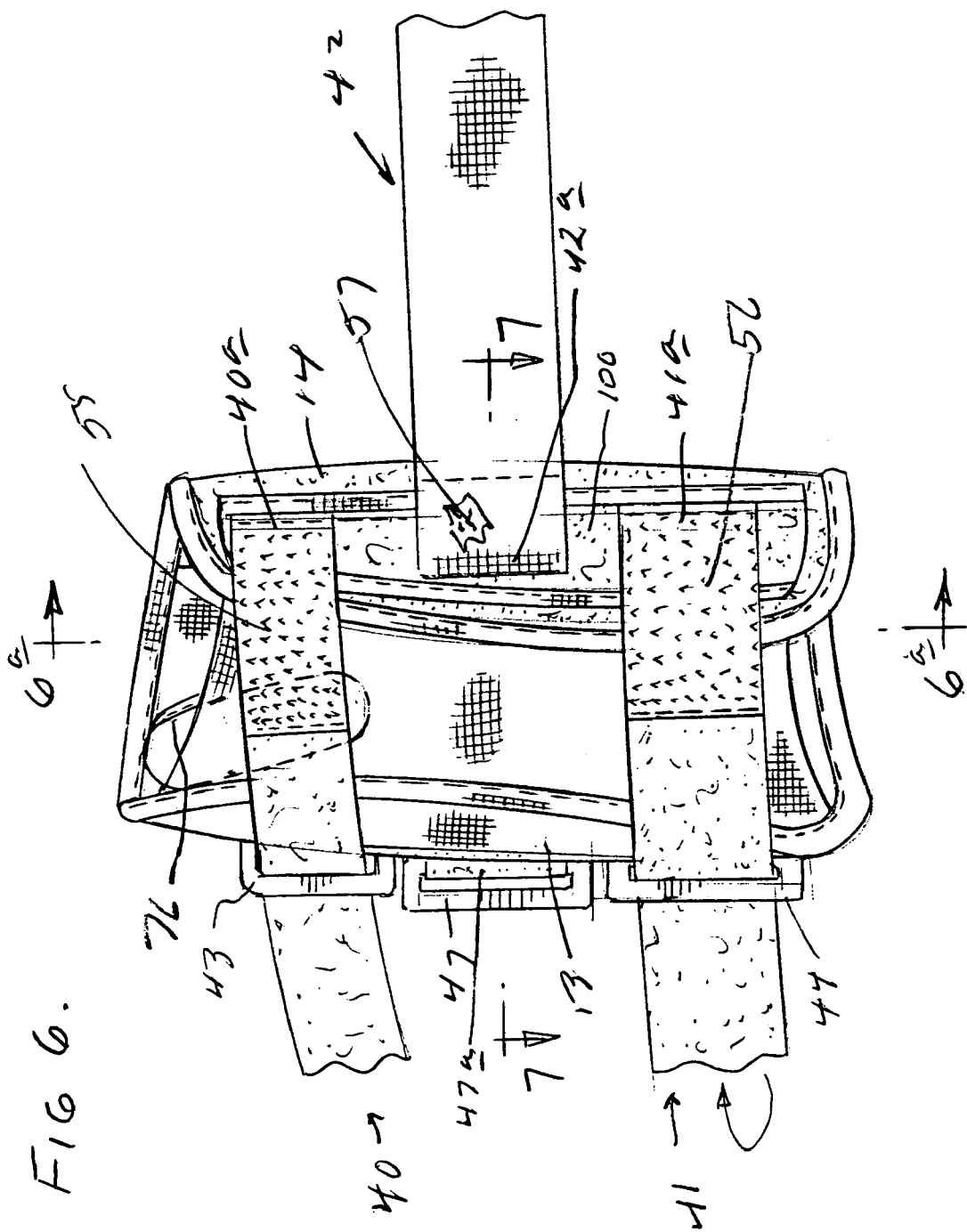
Figure 9:
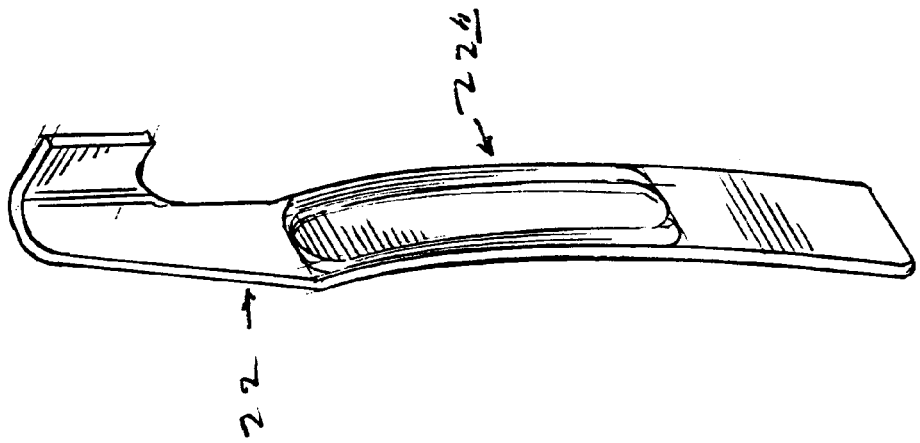
Figure 8:
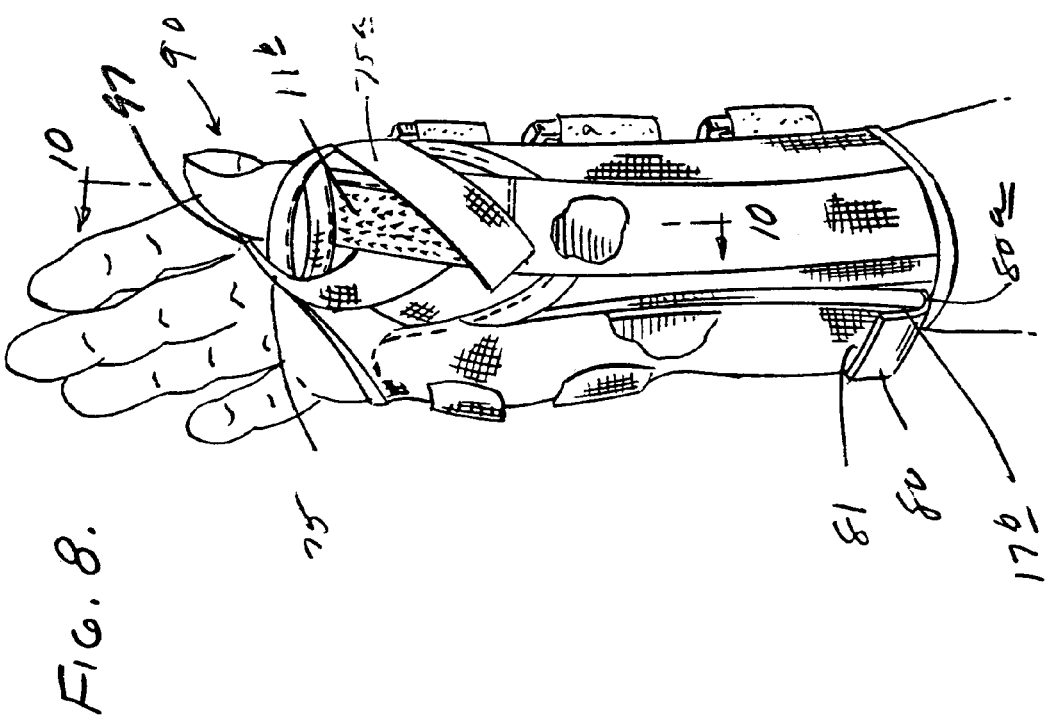
Figure 10:
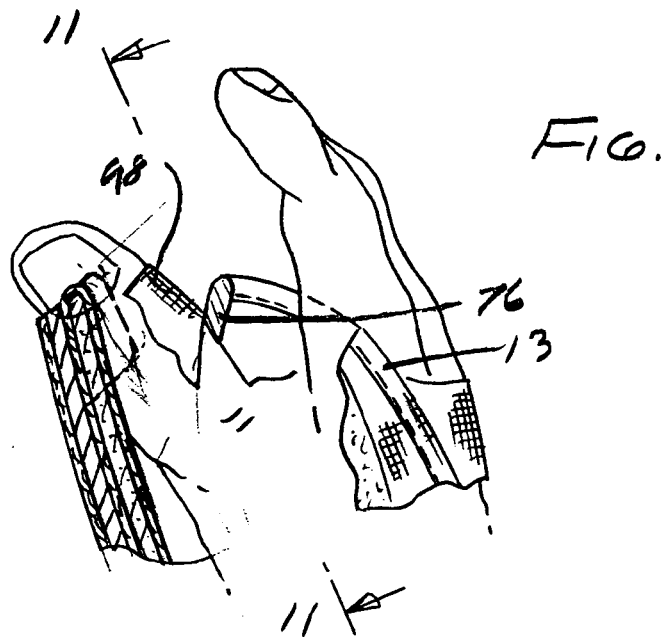
Figure 12:
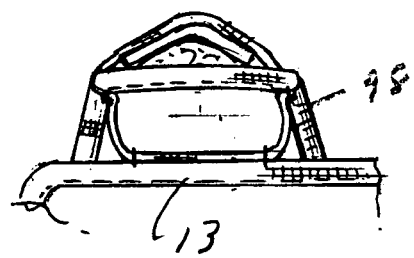
Figure 11:
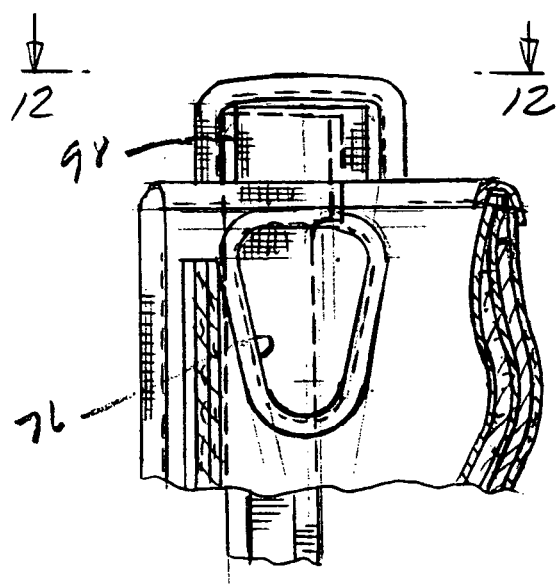
Figure 2:
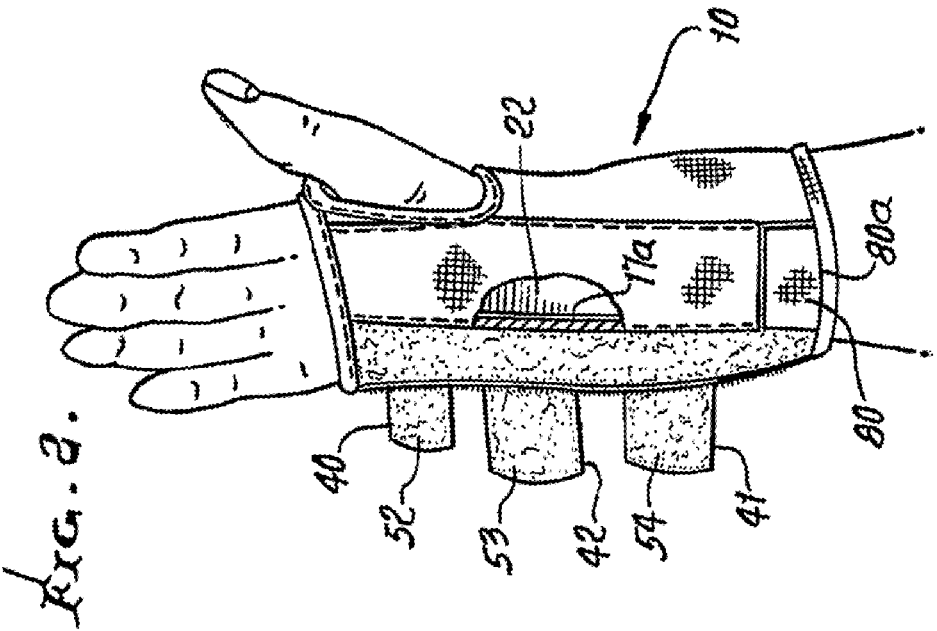
Figure 1:
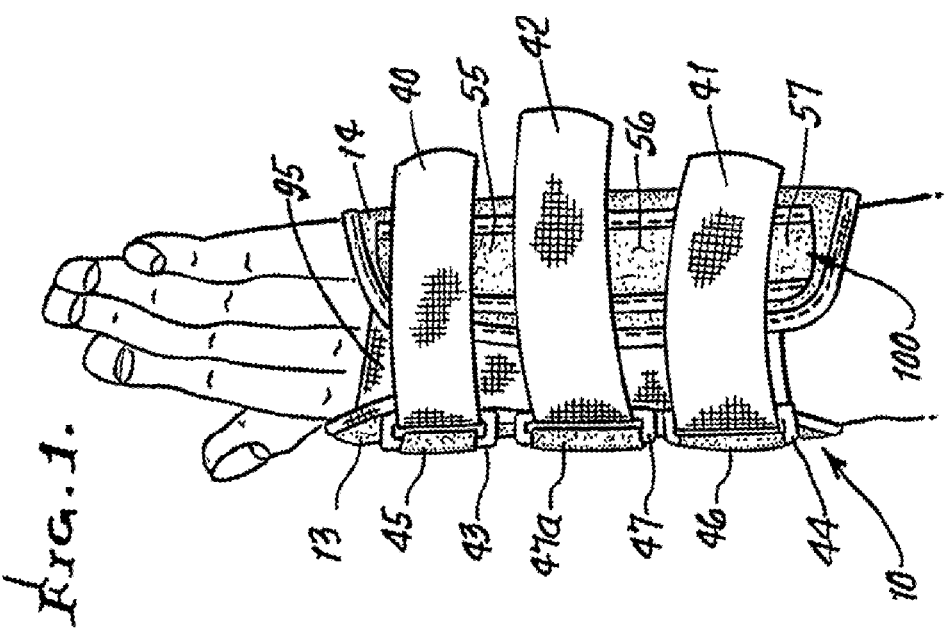
Figure 9:
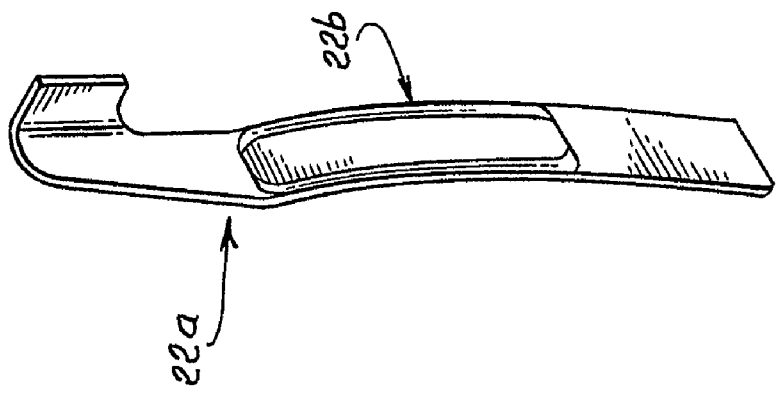
Figure 8:
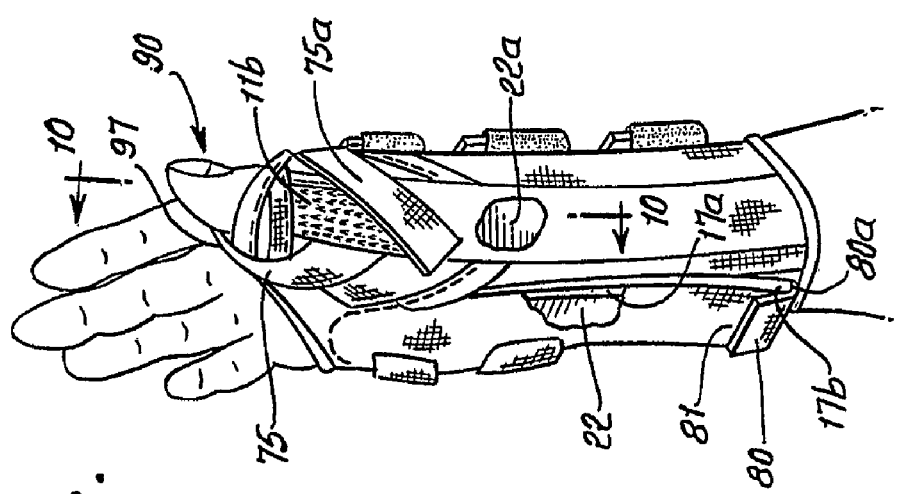
Figure 10:
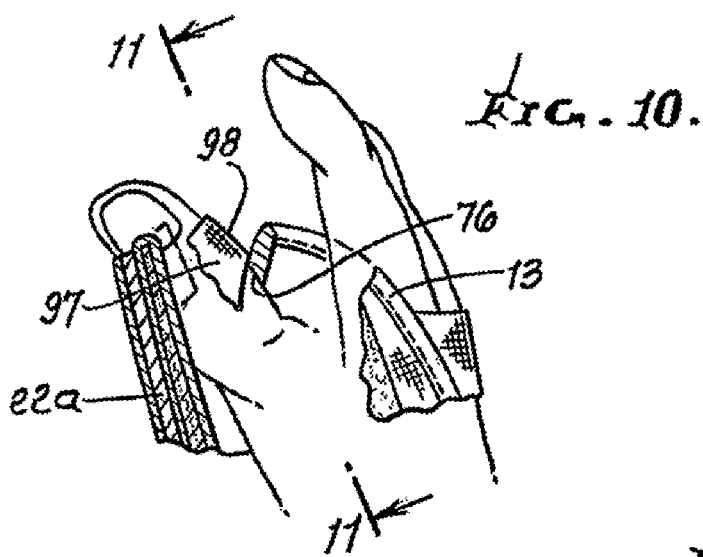
Figure 12:
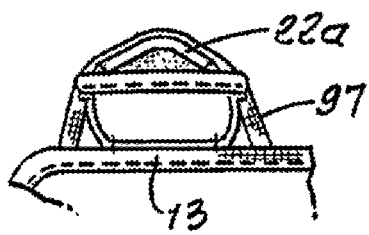
Figure 11:
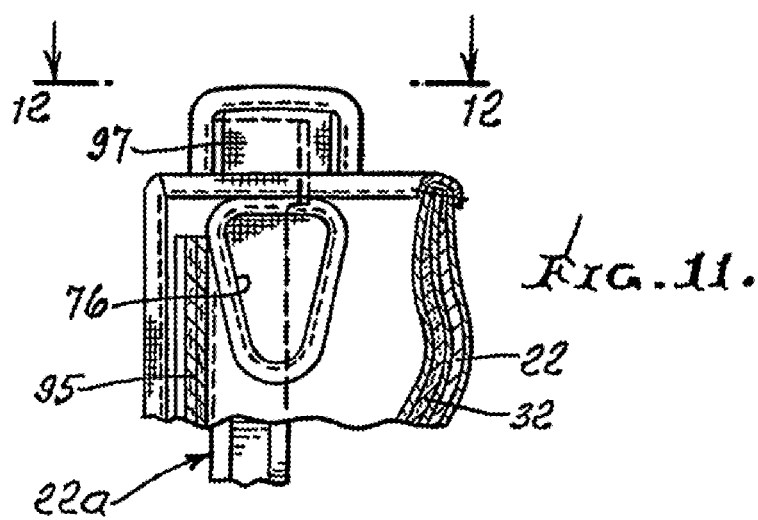

FIG. 1 is an elevation showing the front side of a wrist brace closed and fastened to the user's wrist;
FIG. 2 is like FIG. 1, but showing the rear or inner side of the brace overlying the user's palm;
FIG. 3 is a view like FIG. 1, but showing the brace in opened condition;
FIG. 4 is a view showing opposite side of adjustable strap support;
FIG. 5 is a horizontal section taken on lines 5—5 of FIG. 4;
FIG. 6 is a view like FIG. 3, but showing two straps wrapped to engage buckles;
FIG. 6a is a section taken on lines 6a—6a of FIG. 6;
FIG. 7 is a section taken on lines 7—7 of FIG. 6;
FIG. 8 is a view showing a modified brace completely connected to a wrist;
FIG. 9 is a perspective view of a stiffener;
FIG. 10 is a section taken on lines 10—10 of FIG. 8;
FIG. 11 is a section taken on lines 11—11 of FIG. 10; and
FIG. 12 is a plan view taken on lines 12—12 of FIG. 11.

DETAILED DESCRIPTION

In the drawings, for example FIG. 11, the illustrated wrist brace 10 includes a flexible holder 11 sized to receive the user's wrist 12. The holder includes two flaps adapted to be closed toward one another to secure the holder about wrist 12. See for example flaps 13 and 14, which are vertically elongated and extend to the front side of the holder seen at the back of the wrist in FIG. 1. The flaps may alternatively be tightened toward other portions of the wrist. A stretchable web 95 interconnects 13 and 14, to protect at the outer side of the user's hand. The holder is generally C-shaped or U-shaped in cross section as seen in FIGS. 3 and 7, and has side extents 15 and 16, and a rear extent 17. The holder may consist of flexible durable synthetic sheet material.

Flaps 13 and 14 may typically be stiffened as by vertically elongated stiffeners 18 and 19 received in pockets 13a and 14a; holder side extent 15 may typically be stiffened as by vertically elongated stiffener 20 received in vertically elongated pocket 15a; and holder rear extent 17 may typically be stiffened as by vertically elongated stiffener 22 received in vertically elongated pocket 17a. Such pockets and stiffeners are typically at the outer side of the holder to enhance user wrist comfort. Flexible regions or zones of the holder are shown at 23–26 in FIG. 7, in alternation with the stiffeners pockets, and these accommodate opening and closing of the holder relative to the wrist. Regions 23–26 are vertically elongated, and region 25 defines a non-stiffened pocket between fabric layers 25a and 26b. A resiliently compressible pad 27 is received in that pocket. Preferably, resiliently compressible pads are located in pockets at the inner side of the holder fabric, opposite the stiffeners, as shown. See pad 30 in pocket 30a; pad 31 in pocket 31a; pad 32 in pocket 32a; and pad 33 in pocket 33a. Such locations of the vertically elongated pads and pockets leaves holder fabric zones 23, 24, 25 and 26 free to flex, accommodating closing about the holders wrist, despite the provision and operation of multiple stiffeners and pads.

As referred to, tightening or retention straps are associated with the flaps 13 and 14, as seen for example in FIG. 6, there being at least one first strap 40 having an anchored end 40a at or on a carrier flap 100, and at least one second strap 41 having an anchored end 41a at or on the carrier flap 100. A third strap 42 may be provided, as shown, with an anchored end 42*a* at or on the carrier flap 100. Flap 100 may be, and preferably is adjustably supported on flap 14, as by VEL-CRO connection, allowing variable angling of the straps. Therefore, the three straps 40–42 are gang connected to 100 which is adjustably connected to flap 14.

Also provided are:
i) at least one first loop on the other flap (for example flap 13) to pass said at least one first strap, and at least one second loop on said other flap to pass said at least one second strap, (see for example first and second loops 43 and 44 on flap 13 to pass a first strap 40 and to pass second strap 41, and loop retainers 45 and 46 as seen in FIGS. 1 and 3; and see for example third loop 47 retained at 47*a* to flap 13 to pass third strap 42);
ii) the straps and carrier 100 having connective material thereon whereby the straps can be pulled and tightened after passing through such loops, to adjustably press together on the connective material on the anchored ends of the straps. See connective material such as VELCRO at 52–54 on the straps, and at locations 55–57 on the outward facing surfaces of strap anchoring material. Portions of VELCRO 52–54 may also connect to VELCRO material 58 on the carrier 100, proximate the strap anchored ends, upon fastening of the device to the wrist adding to strap position adjustability. FIGS. 1 and 2 show such fastening, the flaps being closed toward the wrist. See also FIGS. 3 and 6.

FIG. 8 also show optional provision of a thumb strap 75 and 75*a* carried by the holder, to wrap about the base area of the user's thumb 90 projecting from the holder. The strap portions 75 and 75*a* carry hook or pile material to enable thumb strap attachment to pile or hook material on the holder at 11*b*, after being wound about the thumb. FIG. 8 shows that pocket 17*a* for metallic stiffener 22 is open or openable 17*b* near the bottom of the holder, to enable removal of that stiffener, if desired. A short cover flap 80 attached at one end 80*a* to the holder, can be folded upwardly over pocket opening 17*b*, to close it, and VEL-CRO attached to holder, at 81, for retaining the stiffener in upwardly inserted position. Stiffener 22*a* is lengthwise bowed at 22*b*, as seen in FIG. 9, to fit the curvature of the user's palm, adapting to the wrist and palm configuration. Selective endwise removal of the stiffeners from their pockets is enabled, for best fit to a wrist.

It will further be noted in the example that the anchored ends 40*a* and 41*a* of the two straps 40 and 41 are attached to the carrier 100 at two locations spaced along the length of the carrier flap, and that the anchored end 42*a* of strap 42 is attached to the carrier at a location offset from and between those two locations 40*a* and 41*a*.

A secondary band or strap 97 is attached to the holder to receive or extend about the projecting thumb at 90, the base of the thumb projecting through hole 76 in holder.

The loops 43, 44 and 47 are in lengthwise general alignment, to receive the straps, in selected adjusted positions of the carrier 100 adding to adjustability. See FIGS. 1 and 2 and the strap and loop tightening configurations. At least one stiffener, as referred to, is carried by at least one flap and extends lengthwise to extend beneath all three straps. Preferably, at least two such stiffeners are carried by the holder, extending lengthwise thereof, such stiffeners spaced apart about a wrist reception zone defined by the flaps, whereby flexible flap zones are defined between the stiffeners, as referred to. The stiffeners preferably extend beneath all three straps, and beneath cushions, as seen in FIGS. 1 and 2. The stiffeners are typically metallic. More specifically, there are preferably four of said stiffeners, there being cushioning material underlying all said stiffeners, to cushion tightening of the brace about the user's wrist as referred to above.

In FIGS. 4 and 5 straps 40–42 are carried by holder 100; and a stiffener 19 is received in a pocket 14*a*.

FIGS. 6, 10 and 11 show a side opening 76 in the holder to pass the user's thumb.

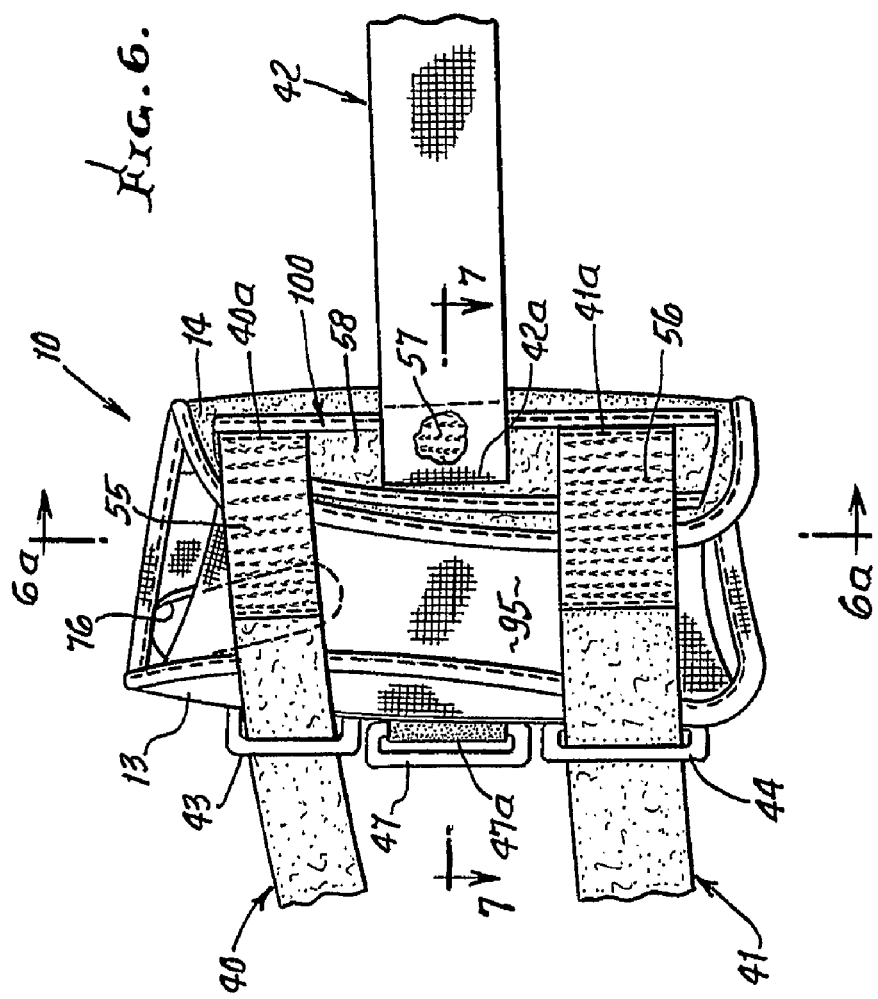

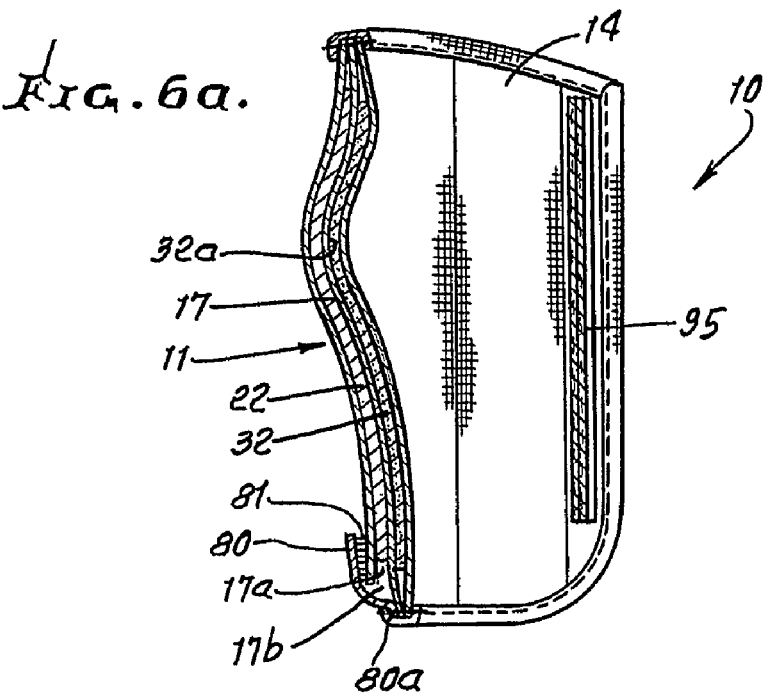
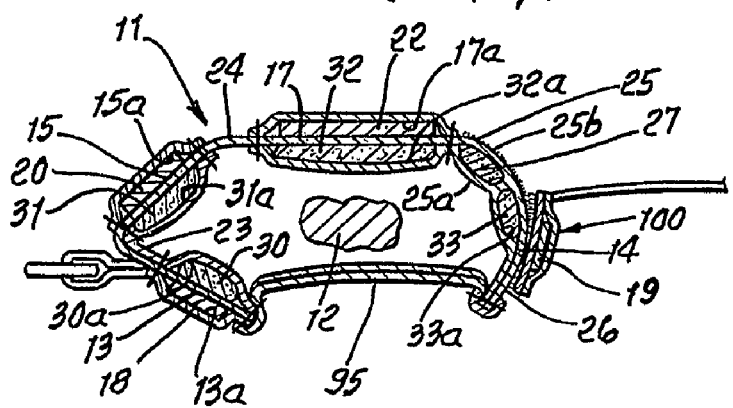

What is claimed is:

1. A wrist brace comprising in combination
   a) a flexible holder to receive the user's wrist and having two flaps adapted to be closed toward one another or toward the wrist to secure the holder about the wrist of the user,
   b) a carrier associated with one flap;
   c) tightening straps associated with said carrier, said straps having ends anchored by said carrier,
   d) loops on the other flap to pass said straps therethrough,
   e) the straps and carrier having connective material thereon whereby the straps can be pulled and tightened after passing through said loops, to adjustably press-together on the connective material on the carrier, and
   f) said carrier being adjustably supported by said one flap.

2. The combination of claim 1 wherein said straps have ends anchored by said carrier.

3. The combination of claim 2 wherein the anchored ends of the said straps are attached to said carrier at locations spaced along the length of said carrier.

4. The combination of claim 3 wherein said loops are in lengthwise alignment.

5. The combination of claim 1 including at least one stiffener carried by a flap and extending lengthwise to extend beneath all three straps.

6. The combination of claim 1 including at least two stiffeners carried by the holder, and extending lengthwise thereof, said stiffeners spaced apart about a wrist reception zone, whereby flexible holder zones are defined between or proximate to the stiffeners.

7. The combination of claim 6 wherein said stiffeners are metallic.

8. The combination of claim 6 wherein there are at least three of said stiffeners, there being cushioning material underlying said stiffeners, to cushion tightening of the brace about the user's wrist.

9. The combination of claim 1 including a flexible auxiliary strap connected to the holder to be adjustably folded over a zone between the user's thumb and forefinger, for adjustable connection to the holder, for firmly attaching the holder in lengthwise position on the wrist.

10. The combination of claim 1 including a flexible auxiliary strap connected to the holder to be adjustably folded over a zone between the user's thumb and forefinger, for adjustable connection to the holder, for firmly attaching the holder in lengthwise position on the wrist.

11. The combination of claim 10 wherein there are three of said tightening straps positioned in spaced relation to the auxiliary strap, when said auxiliary strap is adjustably connected to said connective material on the holder.

12. The combination of claim 1 wherein the flexible holder has U-shape cross-section.

13. A wrist brace comprising in combination
   a) a flexible holder to receive the user's wrist and having two flaps adapted to be closed toward one another or toward the wrist to secure the holder about the wrist of the user,
   b) a carrier associated with one flap;
   c) tightening straps associated with said carrier, said straps having ends anchored by said carrier, d) loops on the other flap to pass said straps,
e) the straps and carrier having connective material thereon whereby the straps can be pulled and tightened after passing through said loops, to adjustable press-together on the connective material on the carrier,
f) and including a flexible auxiliary strap connected to the holder to be adjustable folded over a zone between the user's thumb and forefinger, for adjustable connection to the holder, for firmly attaching the holder in lengthwise position on the wrist,
g) and including a second auxiliary strap carried by the holder to be wrapped about the user's thumb projecting from the holder, and fastened in support position.

14. The brace of claim 1 including a stretchable protective web interconnecting free end portions of the flaps.

15. The combination of claim 5 wherein said stiffener is bowed, lengthwise, and retained in a pocket defined by the holder, in inserted position.

16. A wrist brace comprising a C-shaped holder consisting of flexible sheet material, the holder sized to fit about the wrist, there being multiple stiffeners received in pockets on the holder and extending lengthwise of the holder, and cushioning pads carried by the holder inwardly of the stiffeners, the holder defining flexible zones between successive stiffeners and associated pockets, and retention straps carried by an adjustable carrier flap on the holder to wrap about the pockets and flexible zones for retaining the holder and stiffeners in affixed and adjusted condition to the wrist of the user.

17. The brace of claim 16 including a first auxiliary strap carried by the holder to extend over the region between the user's thumb and forefingers, and fasten to the holder.

18. The brace of claim 17 including a second auxiliary strap carried by the holder to wrap about the user's thumb projecting through a side opening in the holder.

19. The brace of claim 16 wherein there are at least three of said retention straps, and including retention loops carried by the holder to receive said retention straps.

20. The method of using a wrist brace that includes
i) providing the brace of claim 16, and
ii) selectively removing or adding one or more of the stiffeners from or to their associated pockets, to obtain best fit to the user's wrist when the brace is in attached position,
iii) wrapping the retention straps about the remaining stiffeners.

* * * * *

UNITED STATES PATENT AND TRADEMARK OFFICE
CERTIFICATE OF CORRECTION

| | | |
|---|---|---|
| PATENT NO. | : 6,960,176 B1 | |
| APPLICATION NO. | : 10/783008 | |
| DATED | : November 1, 2005 | |
| INVENTOR(S) | : John P. Hely et al. | |

It is certified that error appears in the above-identified patent and that said Letters Patent is hereby corrected as shown below:

The title page should be deleted and substitute therefor the attached title page as shown on the attached page.

Drawings:

Delete drawing sheets 1-6, and substitute therefor the drawing sheets consisting of Figs. 1-12 as shown on the attached pages.

Signed and Sealed this

Eleventh Day of September, 2007

JON W. DUDAS
*Director of the United States Patent and Trademark Office*

United States Patent
Hely et al.

(10) Patent No.: US 6,960,176 B1
(45) Date of Patent: Nov. 1, 2005

(54) REINFORCED WRIST BRACE WITH GANG CONNECTED MULTIPLE STRAPS

(75) Inventors: John P. Hely, Oxnard, CA (US); Martha M. Ortega, Oxnard, CA (US)

(73) Assignee: Weber Orthopedic Inc., Santa Paula, CA (US)

(*) Notice: Subject to any disclaimer, the term of this patent is extended or adjusted under 35 U.S.C. 154(b) by 0 days.

(21) Appl. No.: 10/783,008

(22) Filed: Feb. 23, 2004

(51) Int. Cl.$^7$ .................................. A61F 13/00
(52) U.S. Cl. ........................ 602/21; 602/20; 602/64
(58) Field of Search ...................... 602/5, 20, 21, 602/22, 61, 64; D24/190; 2/162, 170, 16; 128/869, 877, 878, 879

(56) References Cited

U.S. PATENT DOCUMENTS

| | | | |
|---|---|---|---|
| 2,206,404 A | 7/1940 | Jones | |
| 4,854,309 A | 8/1989 | Elsey | |
| 5,307,521 A * | 5/1994 | Davis | 2/22 |
| 5,415,624 A * | 5/1995 | Williams | 602/21 |
| 5,769,804 A | 6/1998 | Harris et al. | |
| 5,982,285 A | 11/1999 | Bueche et al. | |
| 6,024,715 A * | 2/2000 | Maxwell | 602/64 |
| 6,398,748 B1 | 6/2002 | Wilson | |

* cited by examiner

Primary Examiner—Kim M. Lewis
(74) Attorney, Agent, or Firm—William W. Haefliger

(57) ABSTRACT

A wrist brace comprising in combination, a flexible holder to receive the user's wrist and having two flaps adapted to be closed toward one another or toward the wrist to secure the holder about the wrist of the user, a carrier flap on the holder, tightening straps associated with the carrier flap, at the straps having end portions anchored by the carrier, loops on a flap to pass the straps, the straps and carrier having connective material thereon, whereby the straps can be pulled and tightened after passing through said loops, to adjustably press-together on the connective material on the carrier.

20 Claims, 6 Drawing Sheets

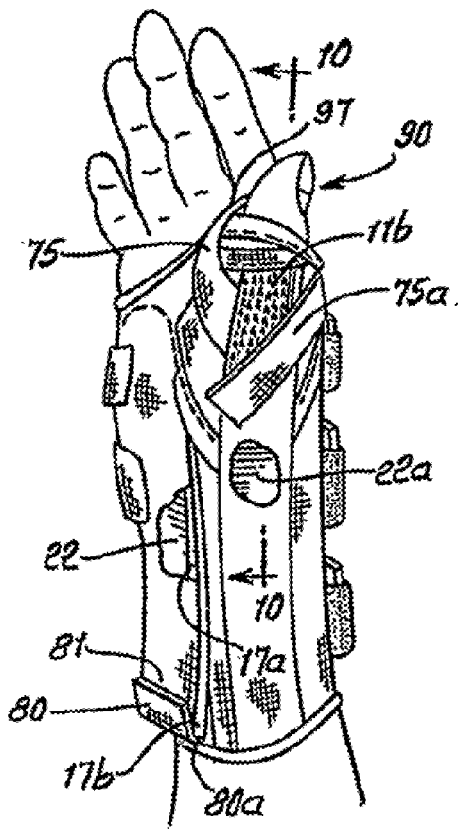

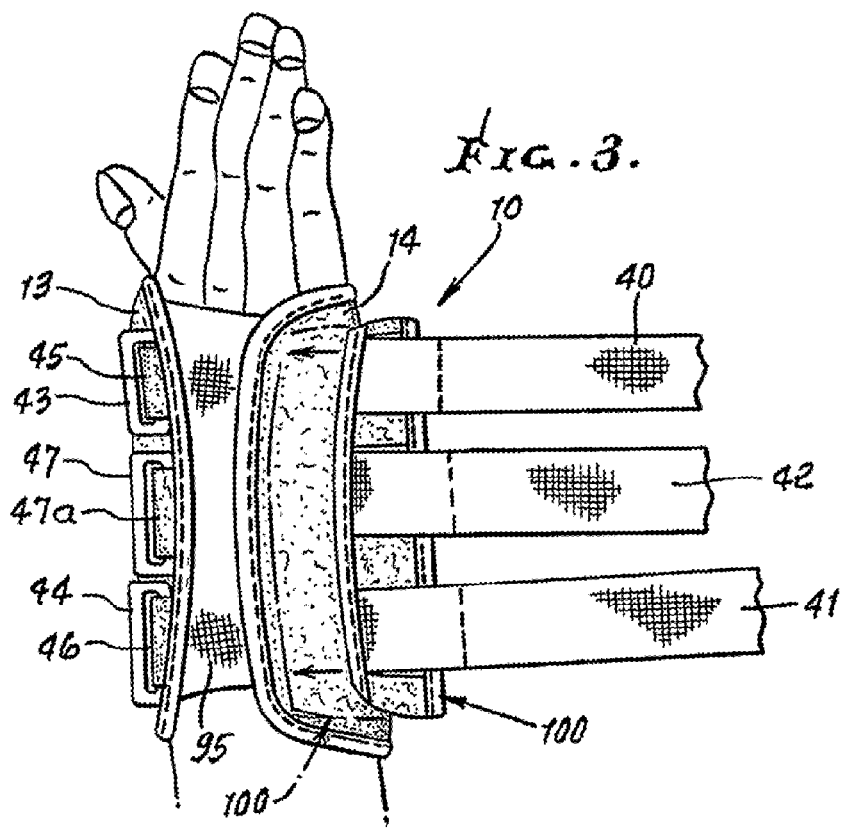
FIG. 3.
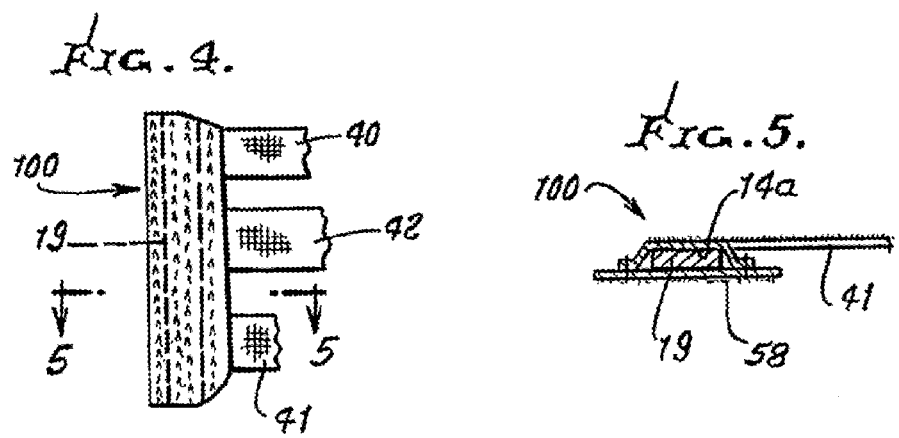
FIG. 4.
FIG. 5.